(12) United States Patent
Coates

(10) Patent No.: US 8,747,380 B2
(45) Date of Patent: Jun. 10, 2014

(54) PROTECTIVE UNDERGARMENT INCLUDING A SLING WITH A POCKET-END CUFF

(76) Inventor: Fredrica Coates, Winston-Salem, NC (US)

( * ) Notice: Subject to any disclaimer, the term of this patent is extended or adjusted under 35 U.S.C. 154(b) by 351 days.

(21) Appl. No.: 13/120,302

(22) PCT Filed: Sep. 22, 2009

(86) PCT No.: PCT/US2009/005264
§ 371 (c)(1),
(2), (4) Date: Mar. 22, 2011

(87) PCT Pub. No.: WO2010/033253
PCT Pub. Date: Mar. 25, 2010

(65) Prior Publication Data
US 2011/0178492 A1    Jul. 21, 2011

Related U.S. Application Data

(60) Provisional application No. 61/192,771, filed on Sep. 22, 2008.

(51) Int. Cl.
*A61F 13/15* (2006.01)
(52) U.S. Cl.
USPC ........... 604/398; 604/393; 604/394; 604/396; 604/397
(58) Field of Classification Search
USPC ..................... 604/393–402; 2/400–408, 238
See application file for complete search history.

(56) References Cited

U.S. PATENT DOCUMENTS

| | | | |
|---|---|---|---|
| 5,137,526 A | 8/1992 | Coates | |
| 5,409,476 A | 4/1995 | Coates | |
| 5,707,364 A | 1/1998 | Coates | |
| 5,722,127 A | 3/1998 | Coates | |
| 5,725,518 A | 3/1998 | Coates | |
| 5,814,037 A | 9/1998 | Coates | |
| 5,891,122 A | 4/1999 | Coates | |
| 6,254,583 B1 | 7/2001 | Coates | |
| 6,579,273 B2 * | 6/2003 | Dupuy | 604/385.14 |
| 6,895,603 B2 | 5/2005 | Coates | |
| 6,926,705 B1 | 8/2005 | Coates | |
| 2001/0016723 A1 * | 8/2001 | Sayama et al. | 604/398 |

(Continued)

OTHER PUBLICATIONS

International Search Report issued in International Application No. PCT/US2009/005264 on Nov. 20, 2009.

(Continued)

*Primary Examiner* — Melanie Hand
*Assistant Examiner* — Aundria Hairell
(74) *Attorney, Agent, or Firm* — Shumaker, Loop & Kendrick, LLP

(57) ABSTRACT

A protective undergarment, such as a diaper, includes a sling that is suspended from an outer shell. The sling forms a pocket in which a reusable or disposable absorbent pad can be positioned. The sling has an S-pocket or overlapping pocket at the front end and a cuff at the rear end. The cuff forms a slimmer outer profile than the S-pocket or overlapping pocket and is used only in the rear where leakage is not as significant as at the front. The S-pocket or overlapping pocket and the cuff are both suspended from bumper strips that extend from the waistband. Rectangular hook and loop fasteners and extension members allow a diaper to fit wearers of different waist size.

20 Claims, 16 Drawing Sheets

(56) References Cited

U.S. PATENT DOCUMENTS

| | | |
|---|---|---|
| 2005/0210560 A1 | 9/2005 | Coates |
| 2008/0103468 A1 | 5/2008 | Elfsberg et al. |
| 2008/0119812 A1 | 5/2008 | Hurwitz |
| 2008/0222781 A1 | 9/2008 | Rhew |

OTHER PUBLICATIONS

Written Opinion of the International Searching Authority issued in International Application No. PCT/US2009/005264 on Nov. 20, 2009.

* cited by examiner

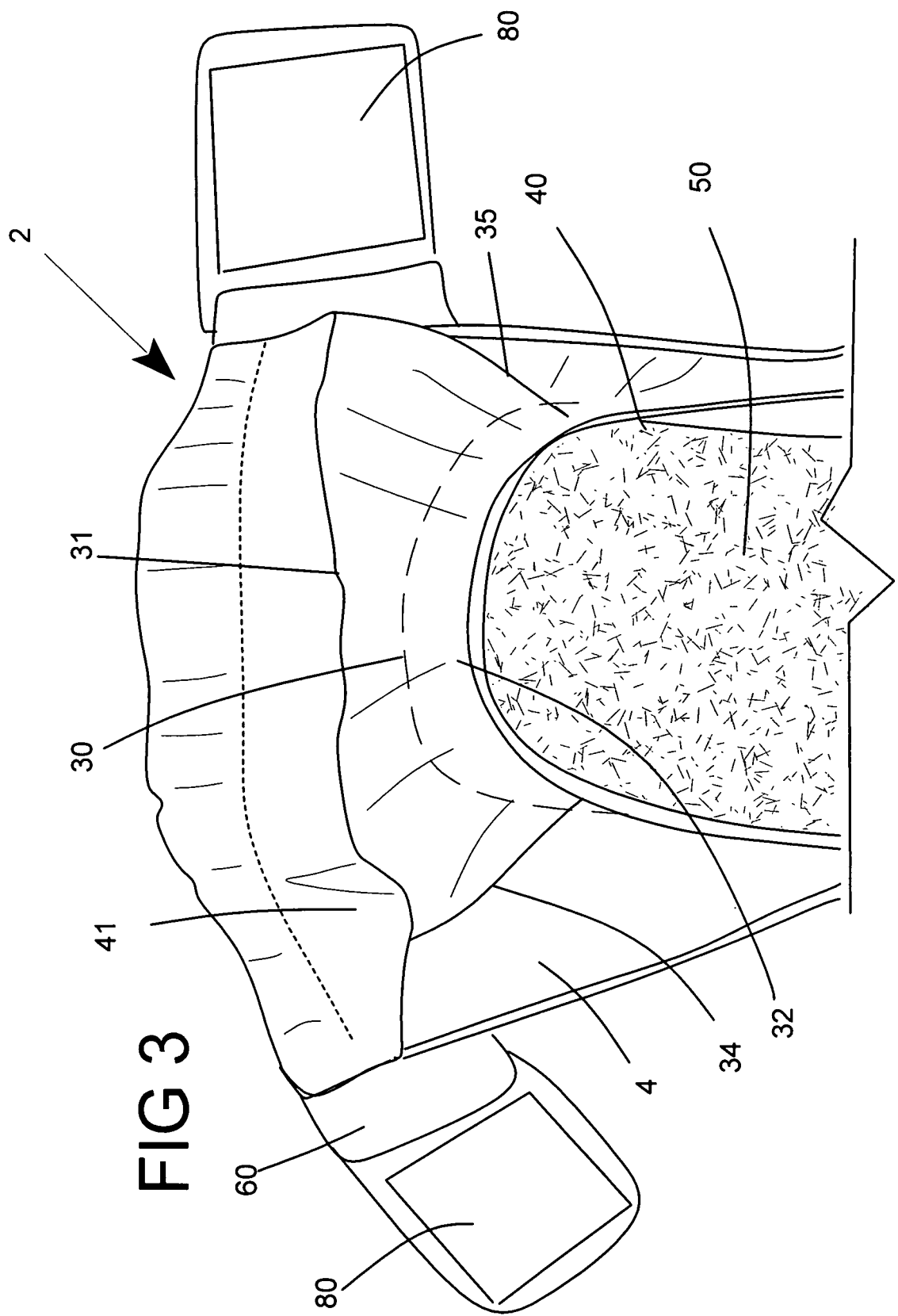

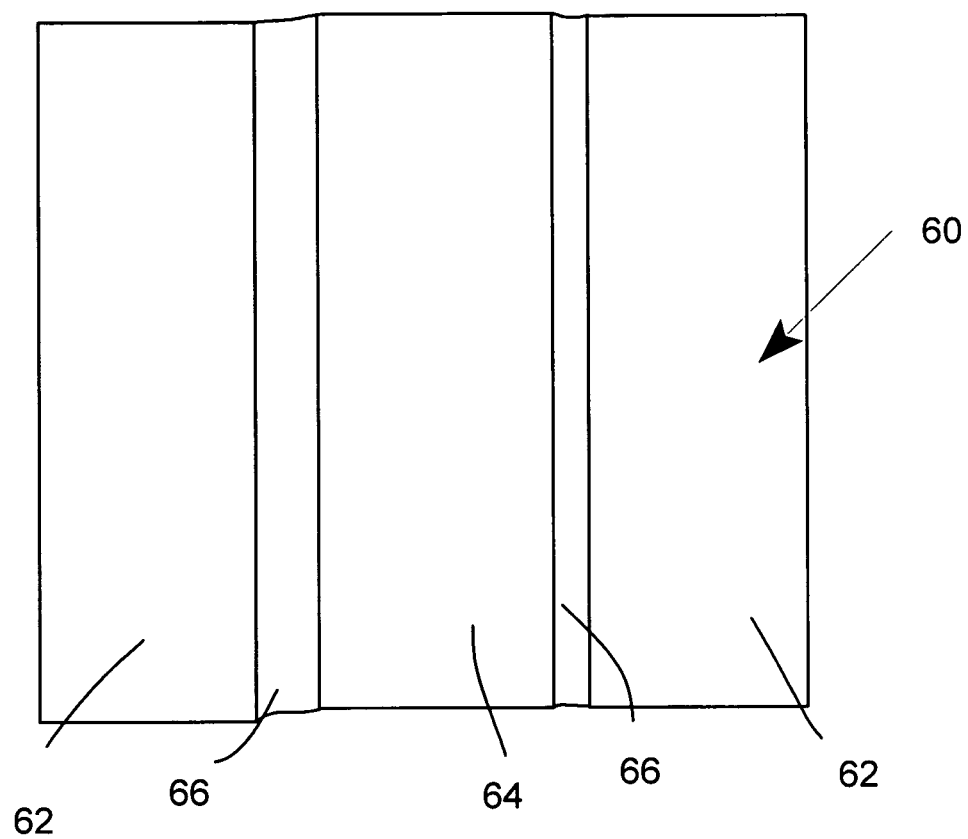

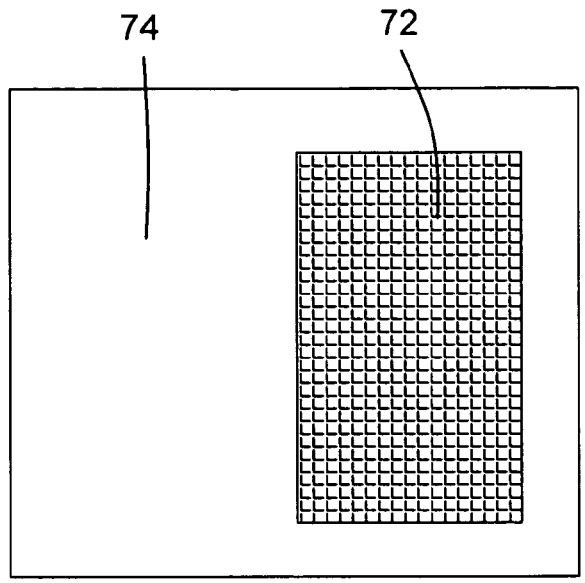
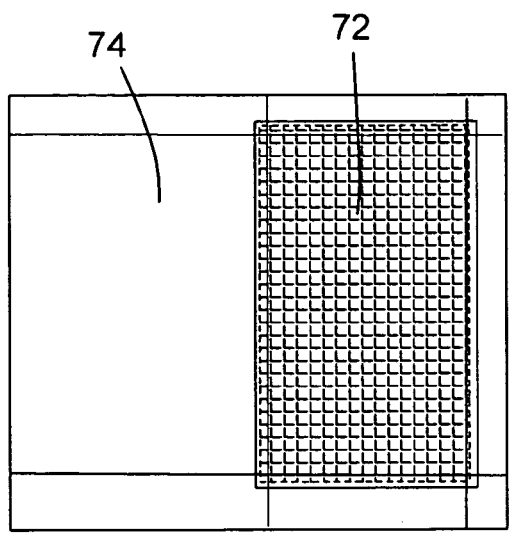
FIG 14A
FIG 14B
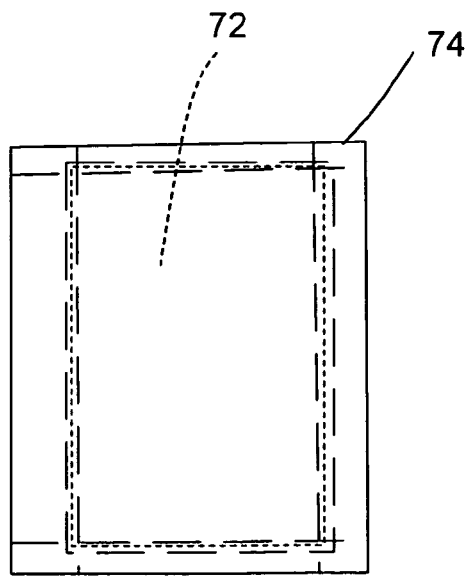
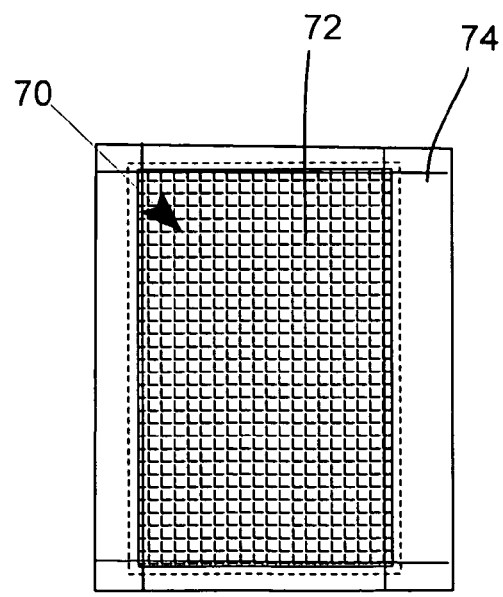
FIG 14C
FIG 14D

PROTECTIVE UNDERGARMENT INCLUDING A SLING WITH A POCKET-END CUFF

BACKGROUND OF THE INVENTION

1. Field of the Invention

This invention relates to protective undergarments that can be constructed in different sizes, and which may be used by adults and children.

2. Description of the Prior Art

Protective underwear having a waterproof or water-resistant sling is shown in U.S. Pat. No. 5,137,526; U.S. Pat. No. 5,409,476; U.S. Pat. No. 5,707,364; U.S. Pat. No. 6,254,583; U.S. Pat. No. 5,722,127; U.S. Pat. No. 6,895,603; and U.S. Pat. No. 6,926,705. U.S. Pat. No. 5,814,037 shows a protective undergarment with a releasable pocket-sling. Front and rear ends of these slings are joined to an outer shell so that the sling can isolate body fluids and fecal matter from the outer shell. A suspended pocketed sling shown in U.S. Pat. No. 6,895,603 is formed by folding front and rear sections of a rectangular fabric about fold lines extending transverse to the major or longitudinal dimension of the rectangular fabric, so that overlapping portions of the rectangular fabric form fore and aft pockets. Exterior crease lines are covered by an elastic trim. Elastic is also placed along side edges to recess and cup the entire frontal potion of the sling to better fit the wearer's anatomy. Stitching along the edges of the pocket holds the three plies of the S-folded fabric construction together. A rectangular pocket opening is thus formed by the transverse fold lines and the longitudinal edges of the rectangular fabric. Remote ends of this pocketed sling can then be attached or stitched to the outer shell, which may be in the form of a pant or a diaper. The sling can hang freely from the opposite ends of the garment, and the absence of stitching between the sling and the garment in the area of the pocket eliminates a leakage path. A disposable pad, either reusable or disposable can be fitted in the pocket, with the ends of the pad held by the fore and aft overlapping or S-shaped sections at opposite ends of the rectangular pocket opening. Although this rectangular pocket can provide a pocket of sufficient volume to collect bodily wastes, and an absorbent pad can be held in place within the pocket, the rectangular opening does not naturally conform to pubic area of the wearer. The exposed material along the crease lines formed by the transverse fold can become soiled compromising the effectiveness of the protective undergarment. This is especially a problem along the front of the undergarment when used for males, especially small boys, because the straight edge of the rectangular opening is wets easily.

In some prior art undergarments formed with S-pockets having rectangular edges, elastic encircles the rectangular sling opening. This elastic pulls material inward and can cause the pocket opening to take on an oval shape with curved front and rear openings. However, this effect of the elastic reduces the size of the pocket opening and provides less, not more, exposure of a disposable pad. This effect thus exposes more of the layer of the sling adjacent to the wearer to the pubic area and increases the area that can be wetted, especially for males. This ovaling effect thus reduces the effectiveness of S-pocket garments formed by a rectangular fold line.

Another approach to forming a pocket on one end of a sling folds opposite sides of the sling on at least one end to form a partially overlapping configuration so that an absorbent pad can be held in place by the partially overlapping sides of the sling. An example of one such configuration is shown in FIG. 13A of U.S. Pat. No. 5,891,122. Another approach to forming a sling pocket for holding the end of an absorbent pad employs drop strips extending along the sides of the sling from the inner surface of the sling to an opening that will be positioned against the wearer. A bumper fabric piece extending around the drop strip on either side forms the pocket along with the overlapped ends of the drop strips. A representative configuration using a bumper fabric piece with drop strips is shown in FIG. 3 of U.S. Pat. No. 5,891,122.

These prior art pocketed slings will retain moisture, and they are therefore especially useful when used on the front of a diaper where water retention is important. However, these pocketed slings can be relatively bulky, resulting in a unsightly bulge in a protective undergarment, especially when used at the rear of the garment, where water retention issues are less demanding than at the front of a protective undergarment. A reduction is the bulkiness of a sling pocket will reduce such bulges. Alternately, a reduction in the bulkiness or thickness of a sling pocket could provide additional space for water absorbent pads. The instant invention will, among other advantages, provide a thinner less bulky sling pocket that can be less bulky, will reduce unsightly protrusions or bulges, and can will allow introduction of water absorbent layers and pads.

SUMMARY OF THE INVENTION

A protective undergarment comprises an outer shell and a sling. The sling includes a main sling layer. The sling is attached to the outer shell along a front end and along a rear end of the sling. Sides of the sling are not attached to the outer shell. Pockets are formed on the front and rear ends of the sling. The pockets are configured to retain opposite ends of a removable fluid absorbent pad extending along an exposed surface of the sling. One of the pockets is formed between a cuff and a main sling layer. The cuff includes two cuff side edges extending between an outer cuff edge and an inner cuff edge. The cuff is stitched to the main sling layer along the outer cuff edge and the two side cuff edges. The inner cuff edge is not attached to the main sling layer and forms one pocket, closed along three sides of the pocket and open along a fourth side of the pocket. One end of the removable fluid absorbent pad can be inserted into the pocket formed between the cuff and the main sling layer.

A protective undergarment according to this invention also comprises an outer shell or garment. A sling has a main sling layer and a second sling layer. The sling is attached to the outer shell or garment along a front end and along a rear end of the sling, sides of the sling not being attached to the outer shell. Pockets are formed on the front and rear ends of the sling. The pockets are configured to retain opposite ends of a removable fluid absorbent pad extending along an exposed surface of the sling. An internal absorbent pad is positioned between the second sling layer and the main sling layer. The pockets are not obstructed by the internal absorbent pad, so that the removable fluid absorbent pad can be employed in addition to the internal absorbent pad.

The protective undergarment of this invention can also comprise an outer garment that is used with a sling that is attached to the outer garment along a front edge and along a rear edge of the sling, with side edges of the sling not being attached to the outer garment. Pockets can be formed on the front and rear of the sling. The pockets would be configured to retain opposite ends of a fluid absorbent pad extending along the surface of the sling. The pocket at the rear of the sling would be a cuff extending over one end of the sling, with the sling and the cuff being stitched to the outer shell along a continuous stitch between opposite sides of the cuff. The pocket at the front of the sling can then be at least partially formed by overlapping layers of a fluid resistant main sling layer.

An alternative aspect of this invention comprises a diaper with an outer diaper cloth shell including a waistband. A sling including a main sling layer is attached to the outer diaper cloth shell along a front end and along a rear end of the sling. Sides of the sling are not attached to the outer diaper cloth shell. Pockets are formed on the front and rear ends of the sling. The pockets are configured to retain opposite ends of a removable fluid absorbent pad extending along an exposed surface of the sling. Rectangular diaper hook and loop fastener members extend from front and rear sections of the outer diaper cloth shell. Each diaper fastener member has a longer dimension extending transverse of the waistband than in a direction along which the waistband extends. Separate rectangular extension members include an extension hook fastener on one surface of a rectangular cloth backing and an extension loop fastener on an opposite surface of the rectangular cloth backing. The extension loop fastener is wider than the extension hook fastener, so that attachment of the extension loop fastener to a diaper hook fastener can be adjusted to provide a fit conforming to different waist sizes of wearers of the diaper.

BRIEF DESCRIPTION OF THE DRAWINGS

FIG. 3 is a view of the cuff on the rear of the pocket, showing how the cuff retains the rear end of the removable fluid absorbent pad.

FIG. 12 shows only the sling, which would be mounted on an outer shell when the second removable fluid absorbent pad would actually be inserted into the diaper.

FIG. 13 is a view of a tri-fold, multi-layer absorbent pad that can be employed in this invention.

FIG. 14A-14D are views showing the construction of the hook fastener used around the waistband to secure the diaper around the wearer. A loop fastening tab located on the rear corners of this protective undergarment.

DETAILED DESCRIPTION OF THE PREFERRED EMBODIMENTS

Figure 1:
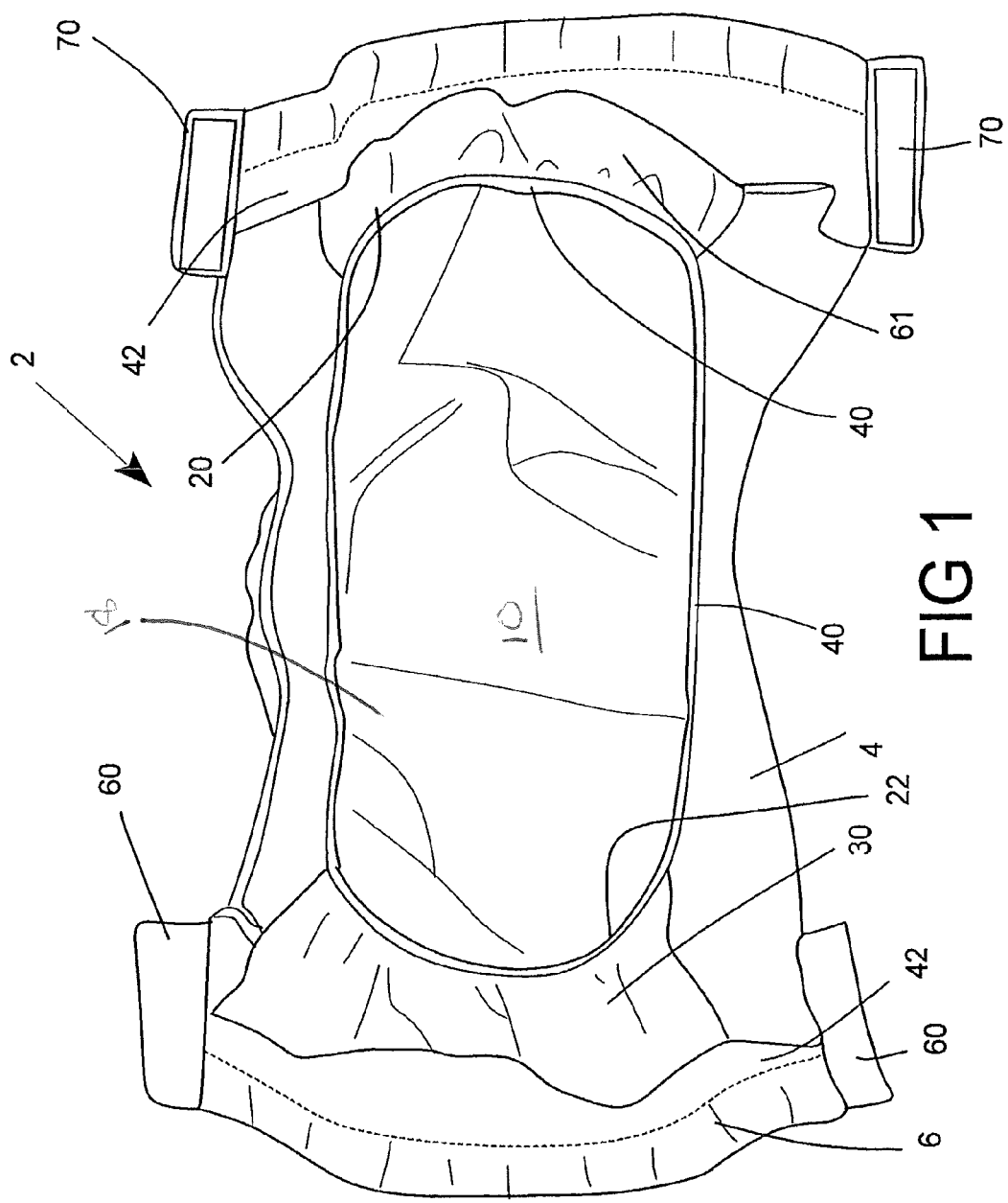
FIG. 1 is a view of a protective undergarment in the form of a diaper having a pocketed sling with an S-pocket on the front of the diaper and a cuff at the rear of the diaper.
Figure 2:
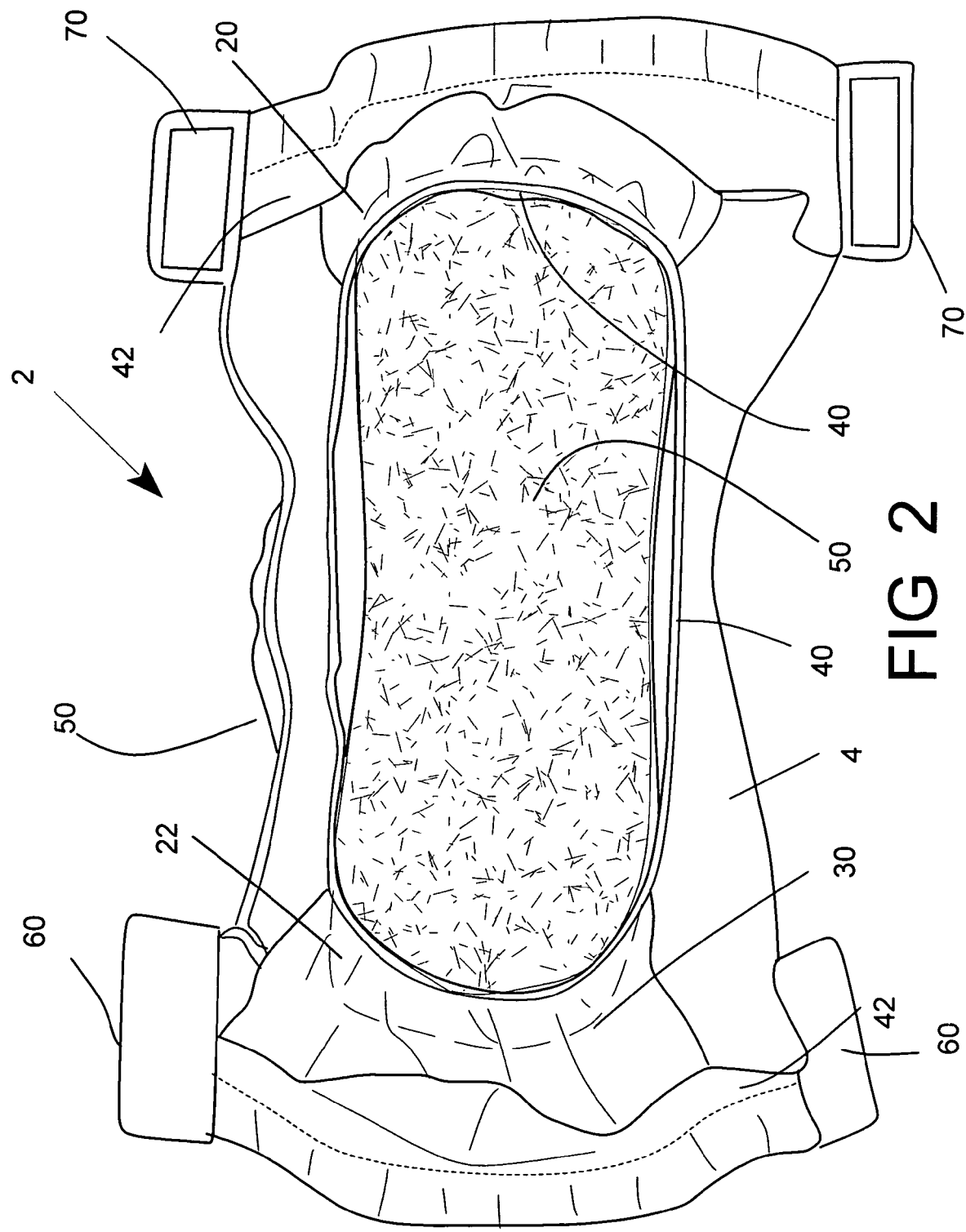
FIG. 2 is a view of the diaper of FIG. 2 with a removable fluid absorbent pad in the pocket.
Figure 4A:
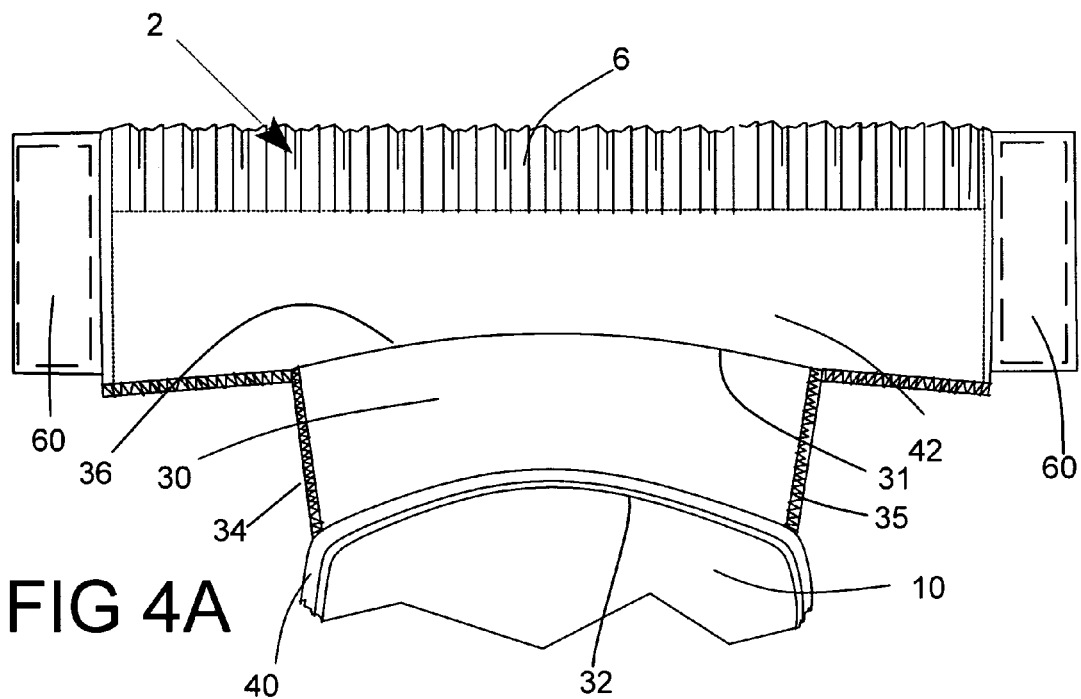
FIG. 4A is a view of the cuff on the rear end of the sling, showing how the cuff is attached to the waistband
Figure 4B:
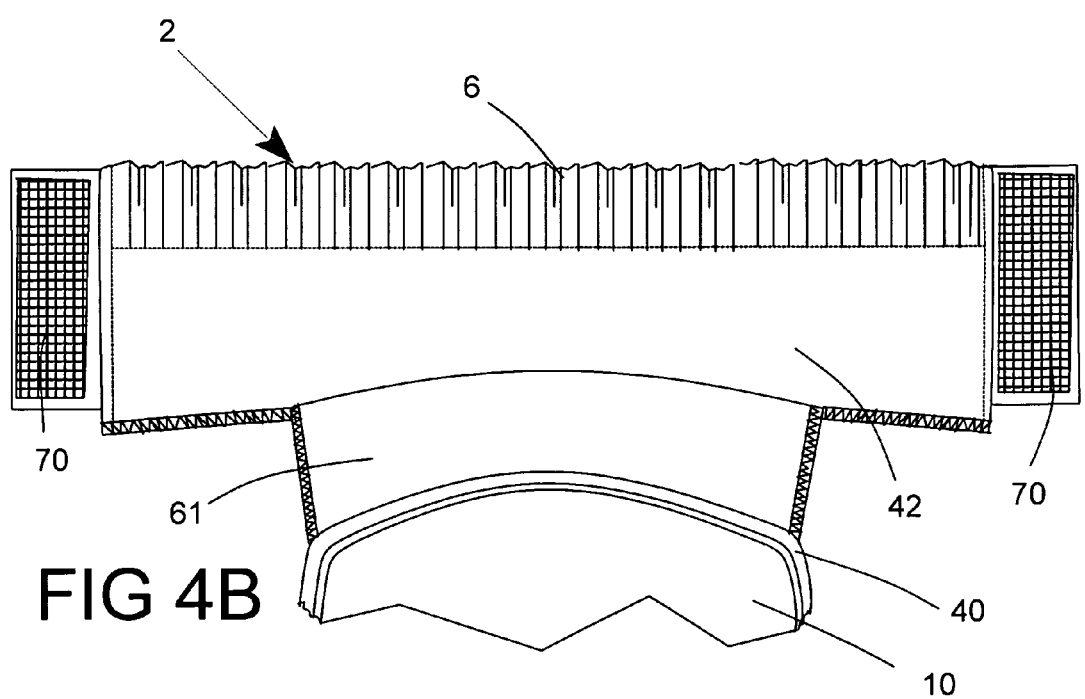
FIG. 4B is a view of the attachment of an S-pocket at the front of the diaper.
Figure 4C:
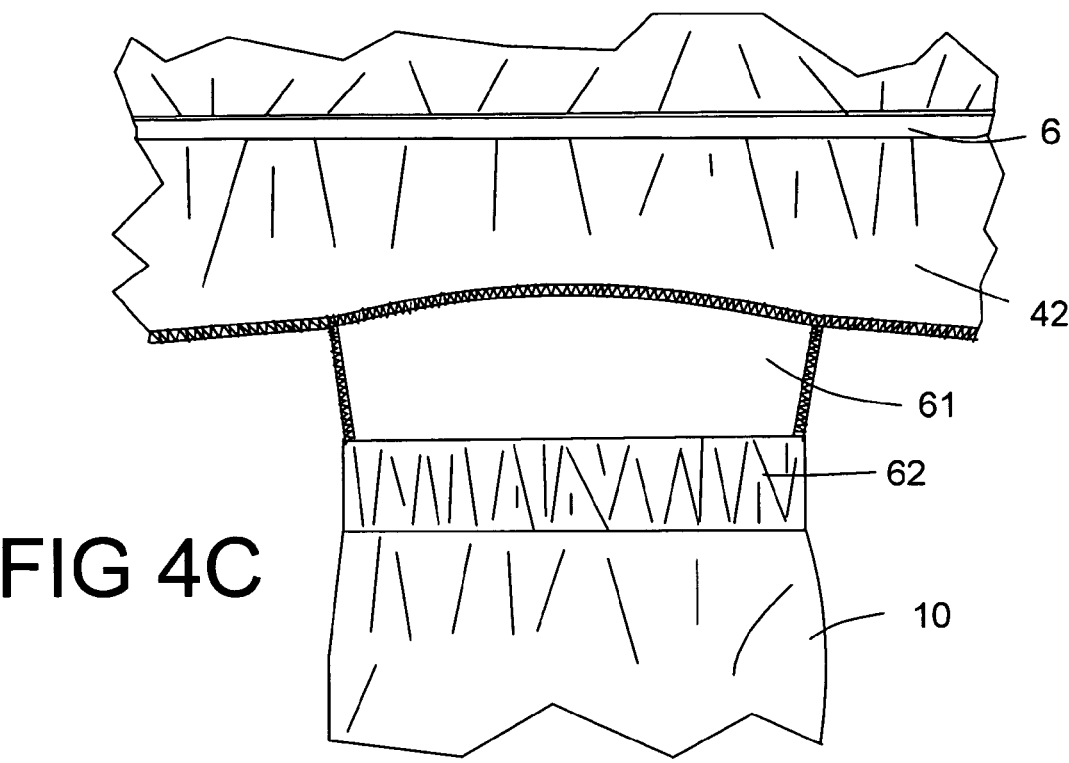
FIG. 4C is a view of the S-pocket, viewed inside out
Figure 4D:
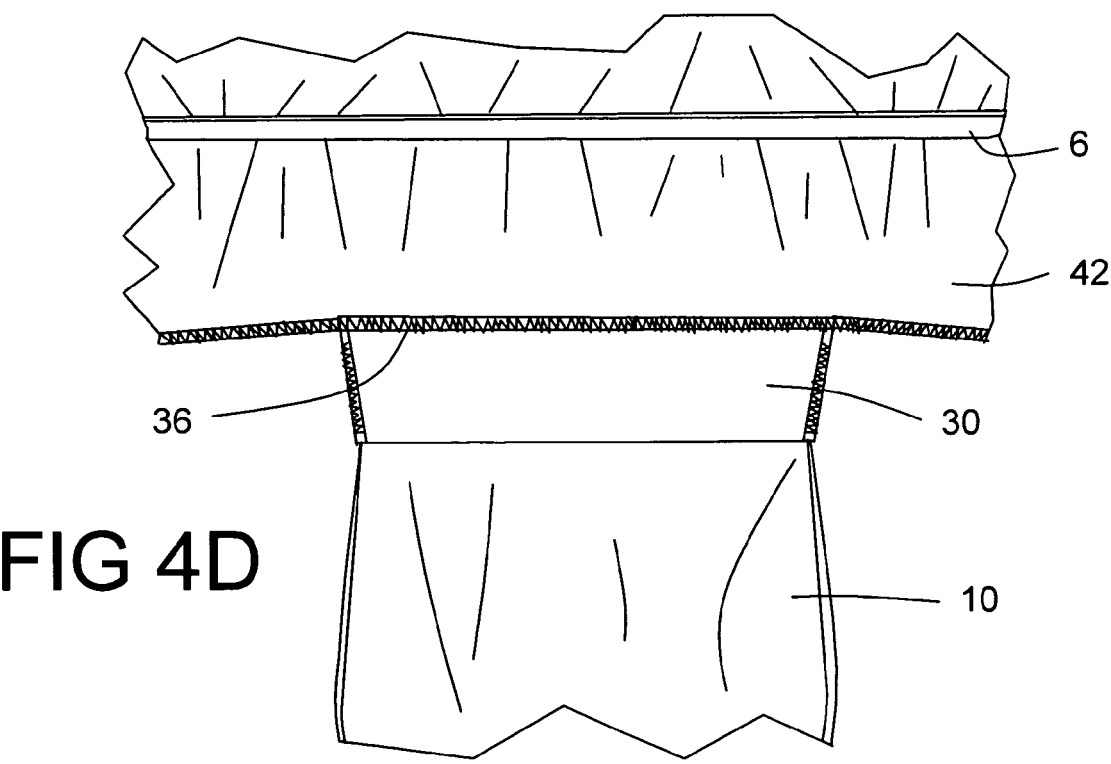
FIG. 4D is a view of the cuff attachment, viewed inside out.
Figure 5:
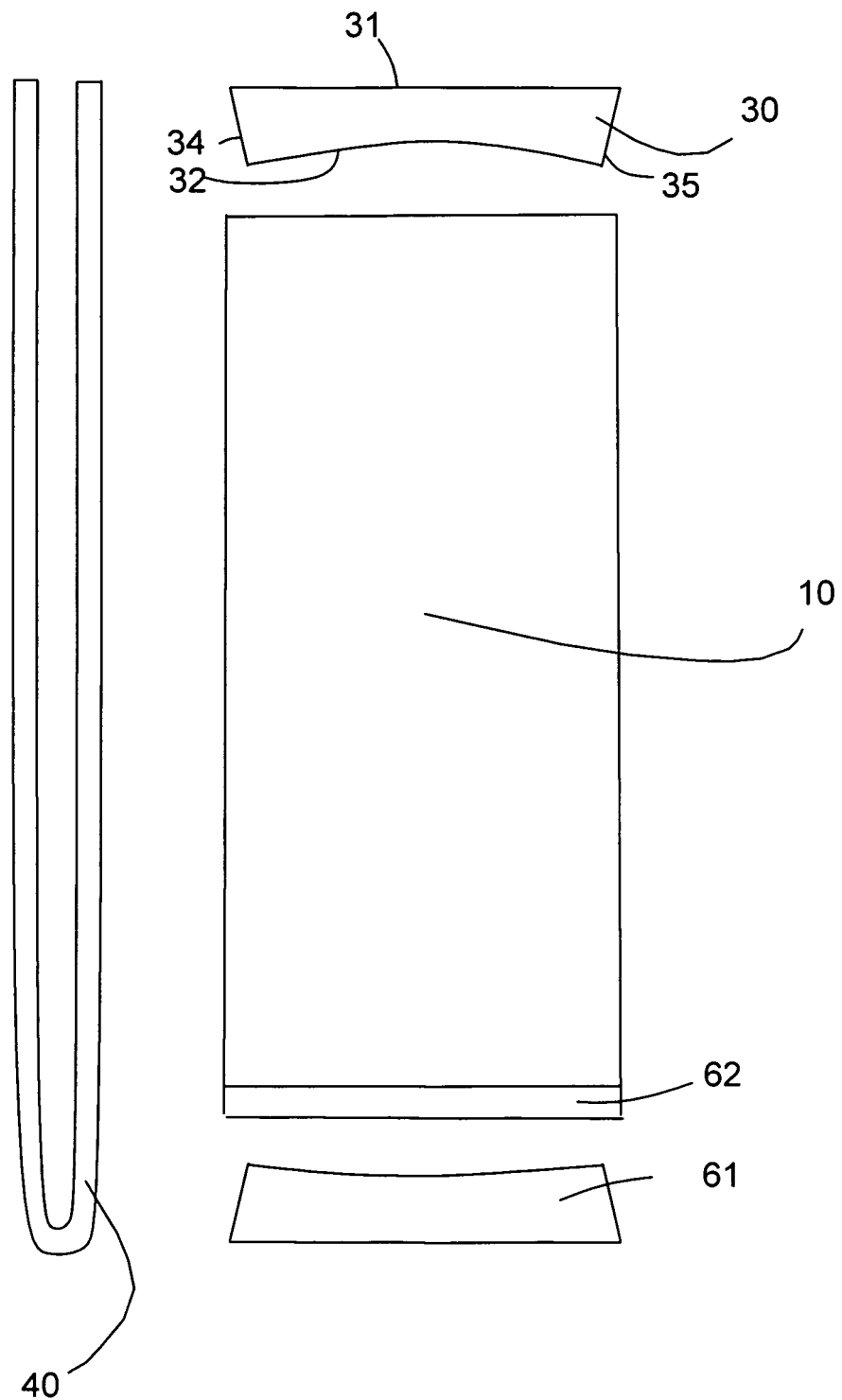
FIG. 5 is view of the component parts of the sling of the embodiment of FIG. 1.
Figure 6:
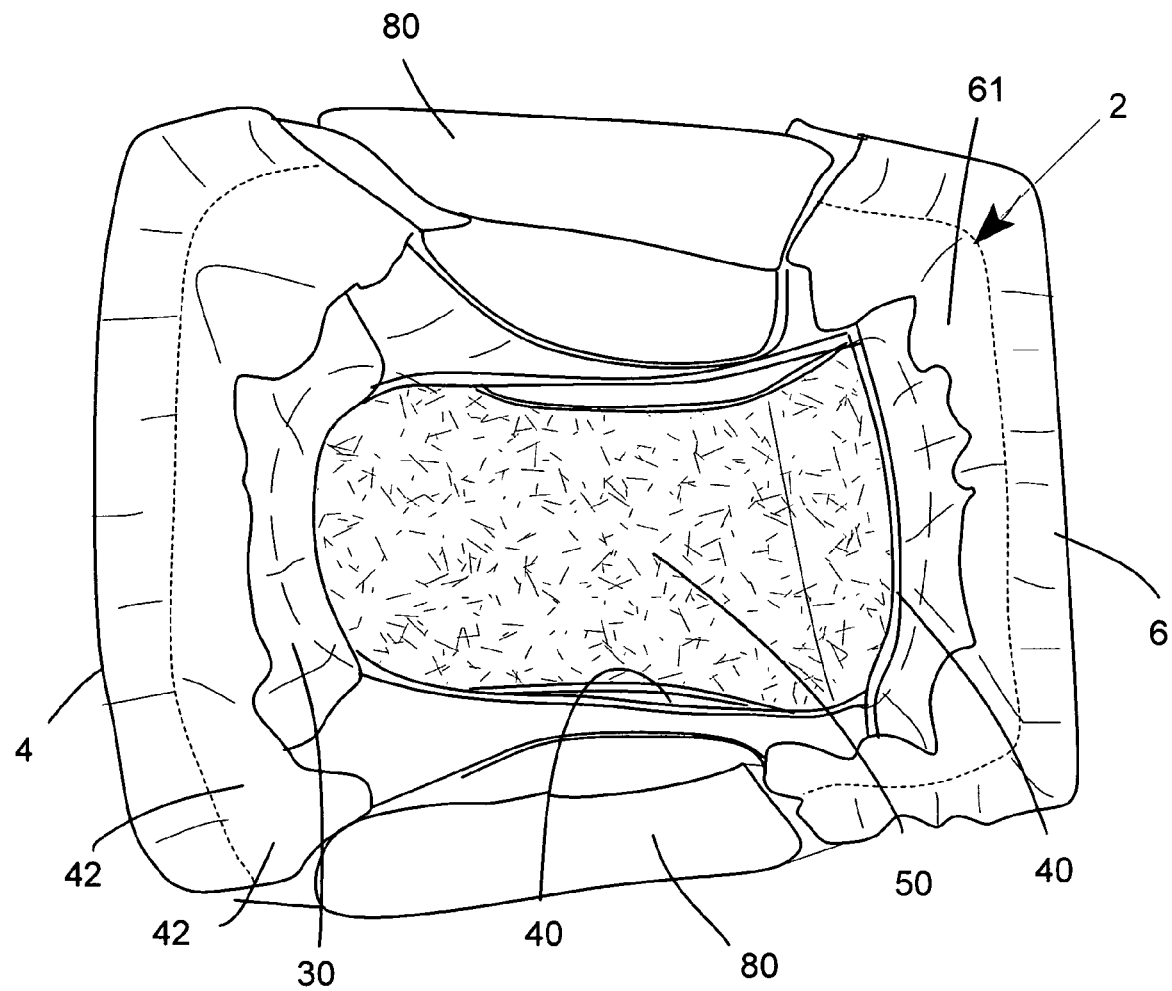
FIG. 6 is a view form above showing how sides of the diaper would be attached when worn. Extender pads that can allow the same diaper to be used to adapt to different sizes are shown.

The version of the protective undergarment 2 of FIGS. 1-15 is in the form of a diaper. Several versions of a diaper in accordance with this invention are depicted, but the same reference number is used to identify primary components, even though modifications to these primary components are incorporated into the different embodiments.

Undergarment 2 can be used with a removable absorbent pad, such as pad 50. The undergarment or diaper 2 has an outer shell 4 with a sling 10 affixed to the outer shell 4 at the front and the rear of the undergarment 2. Sling 10 comprises a pocketed sling having pocket 20, in the form of an S-pocket, formed at the front of the sling 10 and a cuff 30 forming a portion of the pocket 22 at the rear of the undergarment 2. The interior surface of the sling 10 is shown at reference numeral 15. The cuff 30 used in pocket 22 can be referred to as a pocket-end cuff. Bumpers 42 extend from the elastic 8 forming the waistbands 6, and the sling 10 is attached to the bumper 42 at the rear of the undergarment 2 by stitches. The bumpers 42 thus comprise fabric pieces between the waistband and the sling 10 and can reduce the overall length of the sling 10 employed in a specific undergarment. An elastic strip 40 extends around the opening of the sling 10, and will hold the removable absorbent pad 50 in position to absorb moisture. In the first embodiment shown in FIGS. 1-6, the main sling layer 18 is formed of a fluid resistant material, and the outer shell 2 is formed of a softer material, which may be fluid absorbent, but is primarily softer to the touch. The cuff 30, which will be located on the rear of the undergarment 2, need not be fluid resistant, and it too can be formed of a softer material, which will be more comfortable. The bumpers 42 can also be formed of a softer material, since they do not need to be fluid resistant. In this embodiment, the bumpers 42 merely comprise the portions at the end of the fabric forming the outer shell 4. The cuff 30 and the main sling layer 18 are each stitched to the corresponding bumper 42 by a continuous seam 36 that extends from one side of the cuff 30 to its opposite side. This forms a pocket 22 between the cuff 30 and the main sling layer 18 at the rear of the sling 10 and at the rear of the protective undergarment 2.

The sling 10 can have a pocket formed by a soft and water absorbent cuff 30 at the rear portion of the main sling segment 18, because fluid will not be a significant problem at the rear of the sling 10. The front pocket 20, at the front of the sling 10 must contain more moisture, and in this embodiment will comprise an S-pocket formed by three layers of fluid resistant material. The first layer of fluid resistant material is formed by an exposed strip 61 that is sewn to the corresponding bumper 42 and extends to the elastic strip 40, where it is attached to the front edge of the main sling layer 18. The main sling layer 18 is attached to the exposed strip 61 and not directly to the bumper 42, along the inner edge of the main sling layer 18. An elastic strip 40 is sewn around the edge of the sling main layer 18 and along the exposed strip 61. The main sling layer 18 will fold beneath the exposed strip 61 and along with the exposed strip 61 will form an S-shaped pocket in which an end of a removable fluid absorbent pad 50 will be held between fluid resistant material to trap moisture and fluids. This S-pocket forming front pocket 20 will thus prevent leakage at the front of the sling 10 and the protective undergarment 2.

Although the front 20 in the form of an S-pocket provides leakage protection superior to that provided by the rear pocket 22 formed by the cuff 30, such an S-pocket with one end of a removable fluid absorbent pad 50 will be bulkier than the rear pocket formed by the removable fluid absorbent pad 50 extending beneath the cuff 30. However, the rear of sling 10, including pad 50, will form a slimmer shape and the bump that would be formed by the S-pocket will not be as evident at the rear of the undergarment 2. Elimination or reduction of this bump will be especially desirable for protective undergarments intended for use by ladies. Furthermore, reduction of this bump is especially desirable because the superior absorption provided by a multi-layer pad, such as three layer pad 50, is very desirable. Modification of the sling 10, in an area where absorption is not as critical, is preferable to the substitution of a thinner absorbent pad.

Cuff 30 has an outer edge 31 that will be sewn to the bumper 42, which is wider than an inner cuff edge 32 along which the elastic strip 40, forming the periphery of opening of the sling 10, will be sewn. Two inwardly extending cuff side edges 34 and 35 are sewn directly to portions of first and second main sling layer sides 13 and 14 adjacent the corresponding end of the main sling layer 18. The rear end 12 of the main sling layer 18 is sewn to the outer cuff edge 31, and in this embodiment, the stitch line 36 attaching the outer cuff edge 31 to the rear sling end 12 will also attach both the cuff 30 and the main sling layer 18 to the bumper 42. Thus the cuff 30 will be attached to the main sling layer 18 along three edges with one inwardly facing edge forming the top of the rear pocket 22 so that one end of the removable fluid absorbent pad 50 is insertable into the rear pocket 22 as shown in FIG. 3. Since the cuff 30 is sewn directly to the main sling layer 18, the two pieces of fabric will overlie each other to form a thin pocket between opposite cuff side edges 34, 35 and opposite sides of the main sling layer extending under the cuff 30.

In another embodiment of this inventing, shown in FIGS. 9 and 10A-10C, the sling 10 is formed of two layers. The main sling layer 18 formed of fluid resistant material is substantially the same as for a single layer sling, but a second or inner sling layer 19, of substantially the same shape as the main sling layer 18 is added. This second sling layer 19 is preferably a thin fluid absorbent or fluid permeable layer that is stitched to the main sling layer 18 around the periphery of the two layers. However, before attaching the two sling layers around their periphery, an internal fluid absorbent pad 52 is stitched to the second or inner sling layer 19. The internal fluid absorbent pad 52 will thus be a permanent part of this alternate version of sling 10. Although the internal pad 52 will be exposed to moisture passing thought the inner sling layer 19, the outer fluid resistant main sling layer 18 will still retain or trap moisture. A protective undergarment 2 employing a sling with this permanent internal pad 52, can thus be used without the removable fluid absorbent pad 50, especially in situations where it would not be anticipated that a relatively large amount of fluid residue must be retained. The protective undergarment 2 should therefore be more comfortable. However, a removable fluid absorbent pad 50 could still be added, by inserting its ends in front and rear pockets 20 and 22 as with the previous embodiment.

Figure 10A:
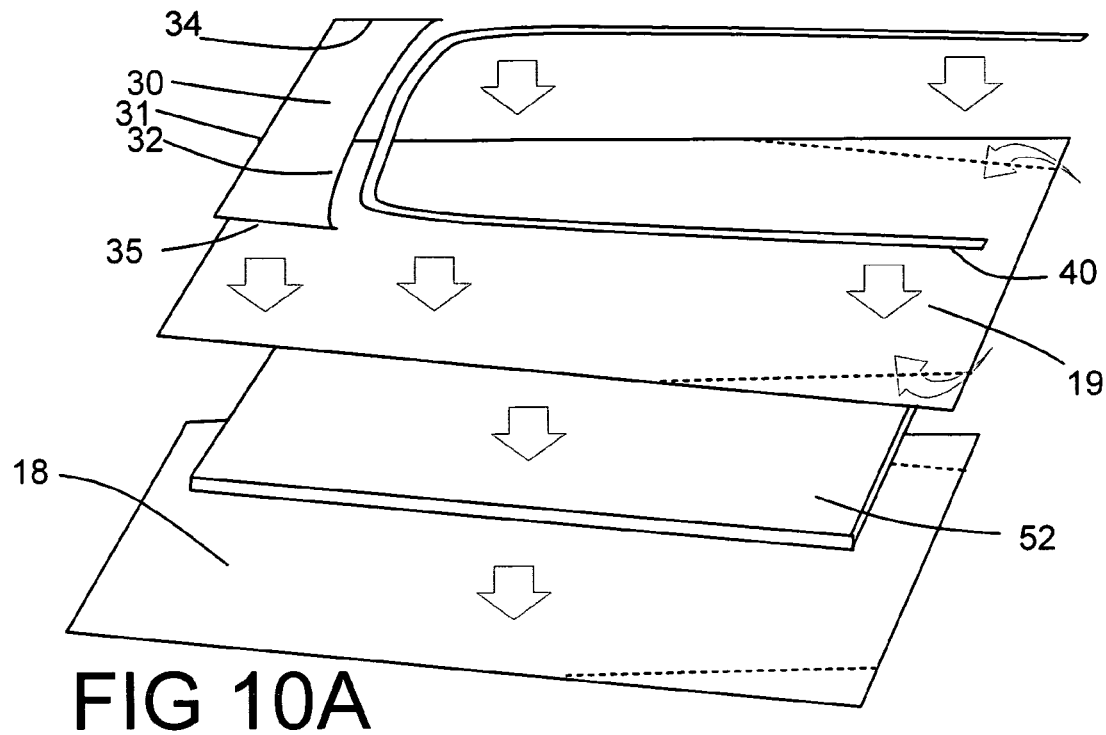
FIGS. 10A-10C shows the components that are used to fabricate the sling employed in the diaper of FIG. 9, also showing the manner of assembling the sling so that the sling can be attached to the diaper shell as an assembled subcomponent.
Figure 10B:
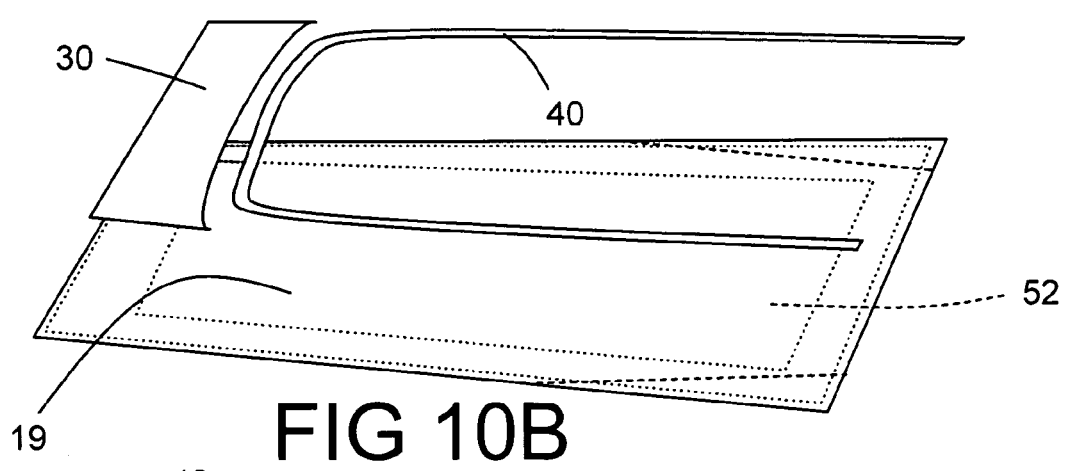
Figure 10C:
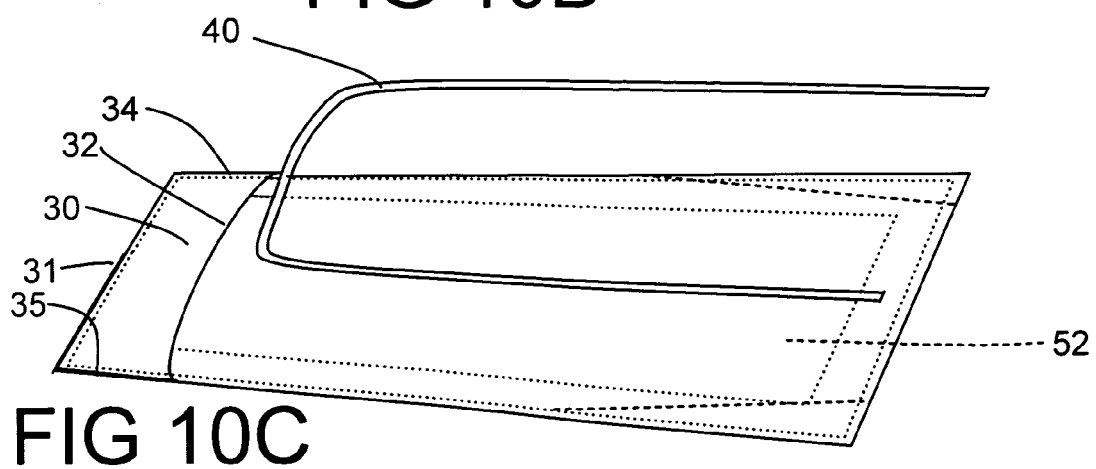

FIGS. 10A-10C show how a sling 10 can be constructed as a separate subassembly that can then be attached to the outer shell 4. The sling as constructed in FIG. 10A-10C would be used in the embodiment of FIG. 9 including the internal pad 52. It should be understood, however, that the same basic assembly and components would be used to fabricate a sling 10 of the other embodiments. For example, the embodiment of FIG. 1 and FIG. 7 would be fabricated in the same manner, but with the elimination of internal pad 52 and the second sling layer 19.

The components shown in FIGS. 10A-10B include a main sling layer 18 that is fabricated from a fluid resistant material. The second sling layer 19 has substantially the same dimensions as the first sling layer 18, but the second sling layer is formed of a material that is either fluid absorbent or a permeable material that will permit fluids to flow through this layer into an internal absorbent pad 52, which is fabricated from a fluid absorbent material. The second or auxiliary sling layer 19 can also be fabricated from a ski friendly material or even a material with an antibacterial agent incorporated therein. The internal pad 52 is sewn to the second or inner sling layer 19, as shown by the stitch lines surrounding the internal pad 52 in FIG. 10B.

After the internal pad is sewn to the second or inner layer 19, the main or outer sling layer 18 is sewn around its edges to the second sling layer 19 with the pad 52 attached thereto. Pad 52 would not be sandwiched between the two sling layers 18 and 19. After this step, shown in FIG. 10B, the cuff 30 will then be stitched on the inwardly facing surface of second sling layer 19. It should be understood that if a smaller internal pad 52 had been employed, the cuff 30 could be stitched to the second or inner sling layer 19 before the pad 52 was attached thereto, because there would then be sufficient clearance for stitching the pad 52 to the second sling layer 19, without stitching through the overlying cuff 30.

The cuff 30 is stitched to the composite formed by sling layers 18 and 19 and internal pad 52 by stitching along cuff side edges 34 and 35 and along the outer end cuff edge 31. This may be one continuous stitch. The inner cuff edge 32, which in the preferred embodiment is arcuate or curved, is not sewn to the sling layers 18, 19 but remains open to form the pocket covered by cuff 30. See FIG. 3 for a view showing the cuff 30 after attachment to a outer shell 4. Note, that the cuff 30 will overly the sling layer 19, without any folds, so that a thin pocket, with no excess layers is formed.

An elastic strip 40 is then stitched to the side edges of the composite sling subassembly of FIG. 10C, and this elastic strip 40 will continue around the curved cuff inner edge 32. The elastic will then draw the edges of the sling layers 18, 19 and the cuff inwardly so that a removable internal pad 50, with pad edges extending under the cuff 30, can be held in the pocket. It should be understood that separate elastic strips can be employed. For example, elastic strip could extend along the side edges of the sling layers 18, 19, and a separate elastic strip could extend along the curved cuff edge 32.

Figure 7:
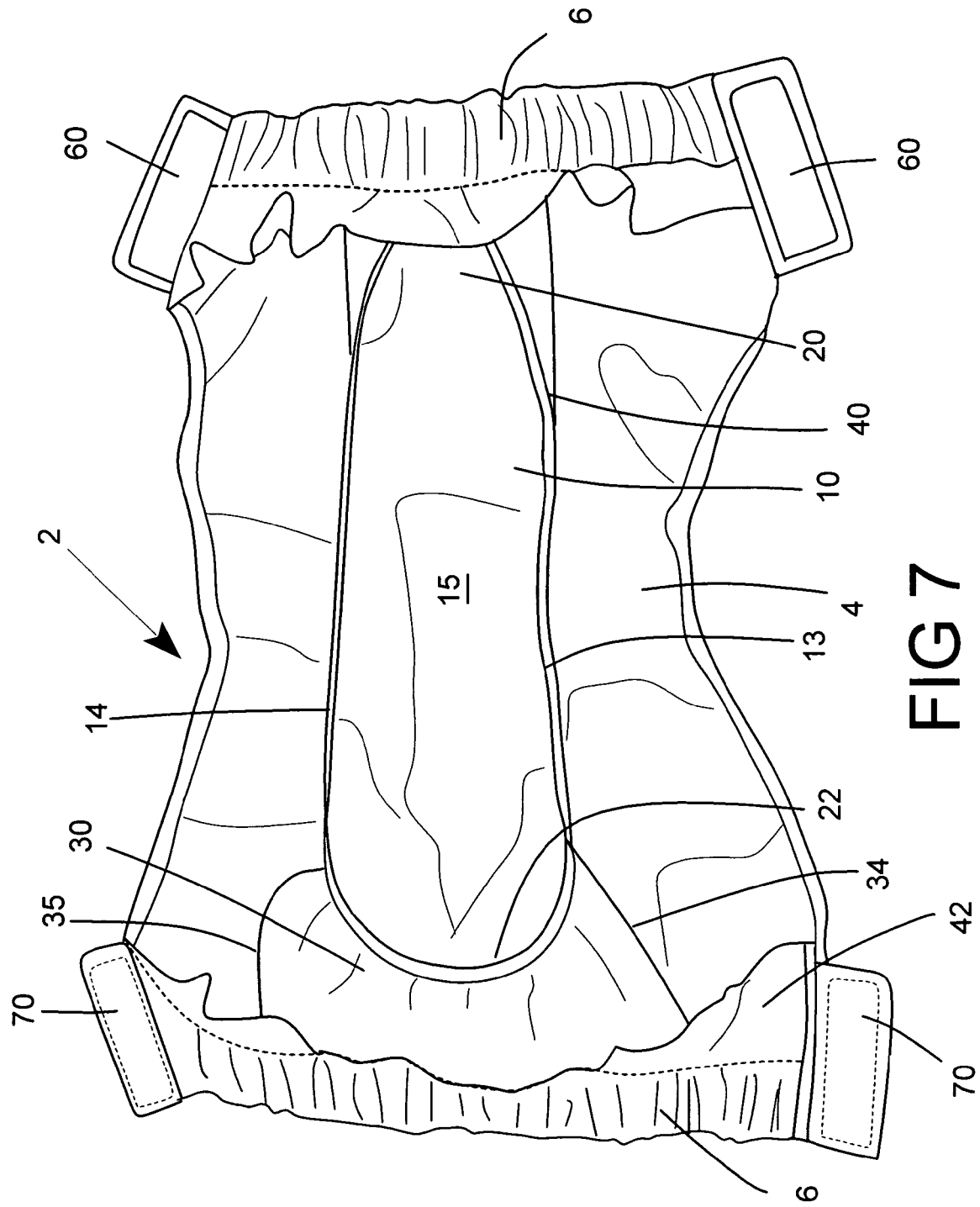
FIG. 7 is a view of an alternate embodiment of a protective undergarment in form of a diaper in which an overlapping configuration forms a front pocket and a cuff forms the rear pocket.
Figure 8:
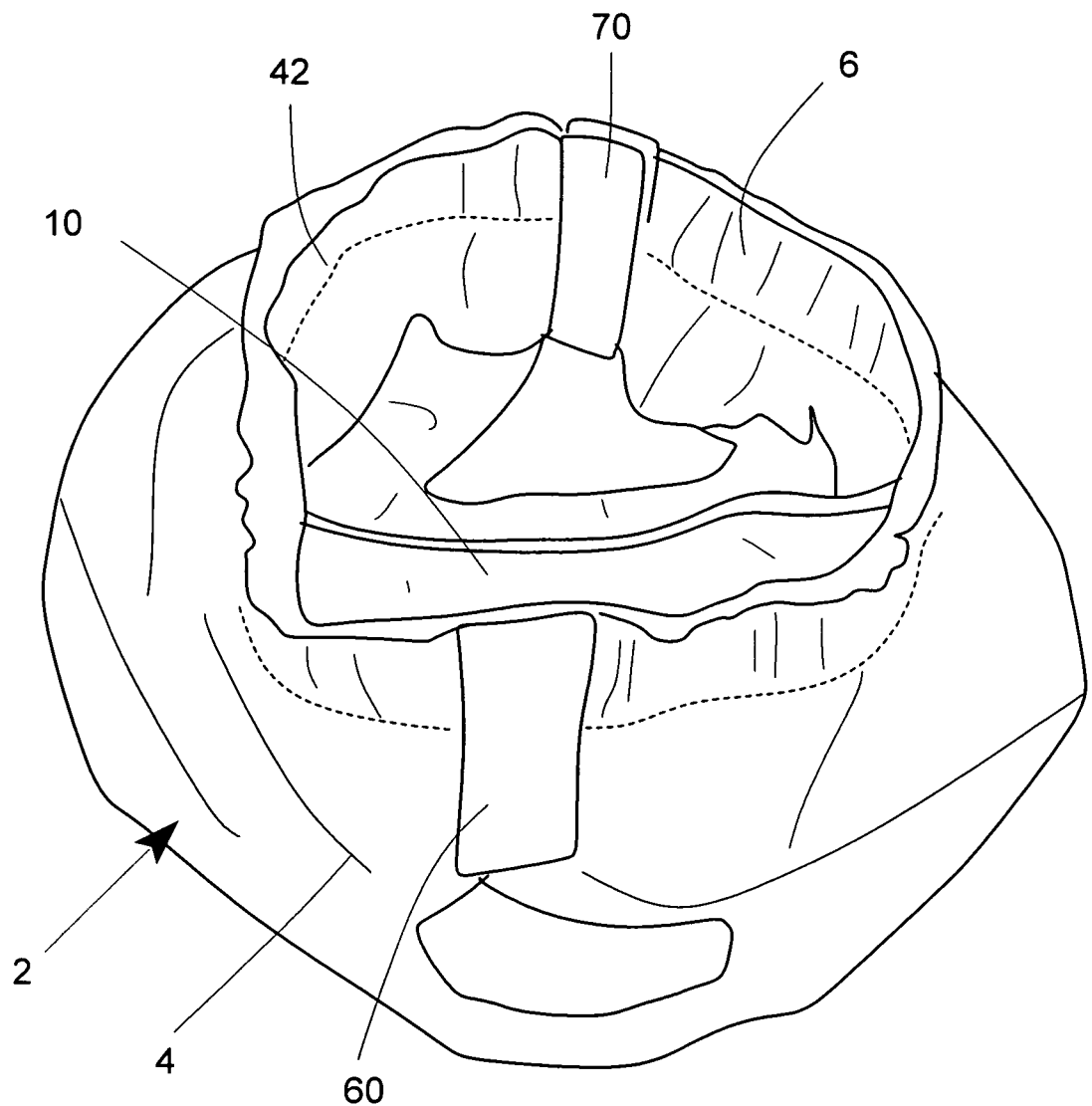
FIG. 8 is a view of the diaper of FIG. 7 as it would be worn.
Figure 9:
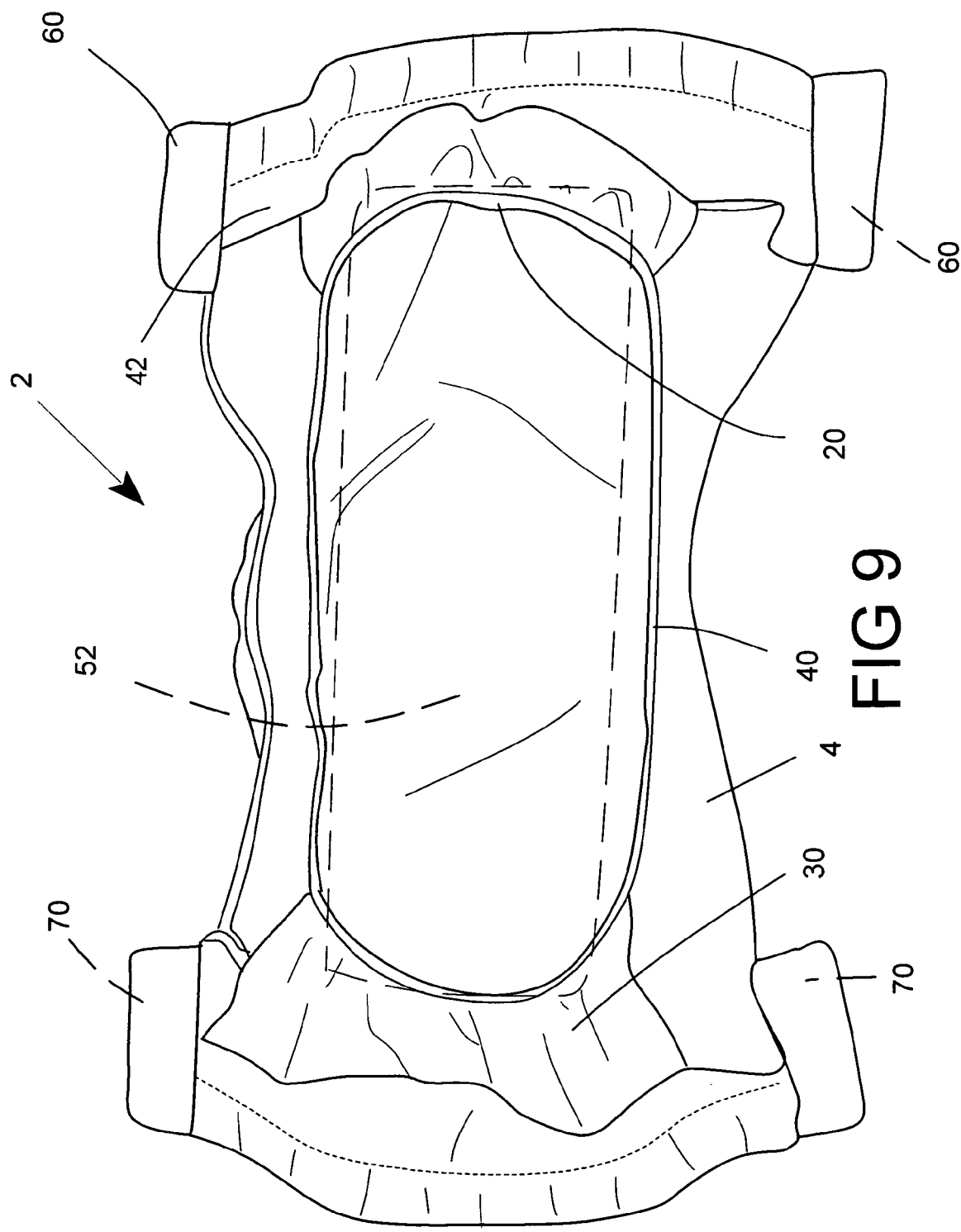
FIG. 9 is a view of a pocketed sling diaper according to this invention is which an internal fluid absorbent pad is sewn into the sling.

FIGS. 10A-10C show the construction of sling 10 that would be used in the embodiment having overlapping side edges at the front of the sling, such as that shown in FIG. 7. Note that the elastic strip 40 ends at the front end of the sling, opposite from the rear sling end, where the cuff is attached. The dashed lines shown on the front ends of sling layers 18 and 19 show how these layers would be overlapped for attachment to the outer shell to form a overlapping pocket. Substantially the same construction technique could be employ to form an S-pocket at the front end. The elastic strip 40 would then extend around the front end of the sling 10.

Figure 11:
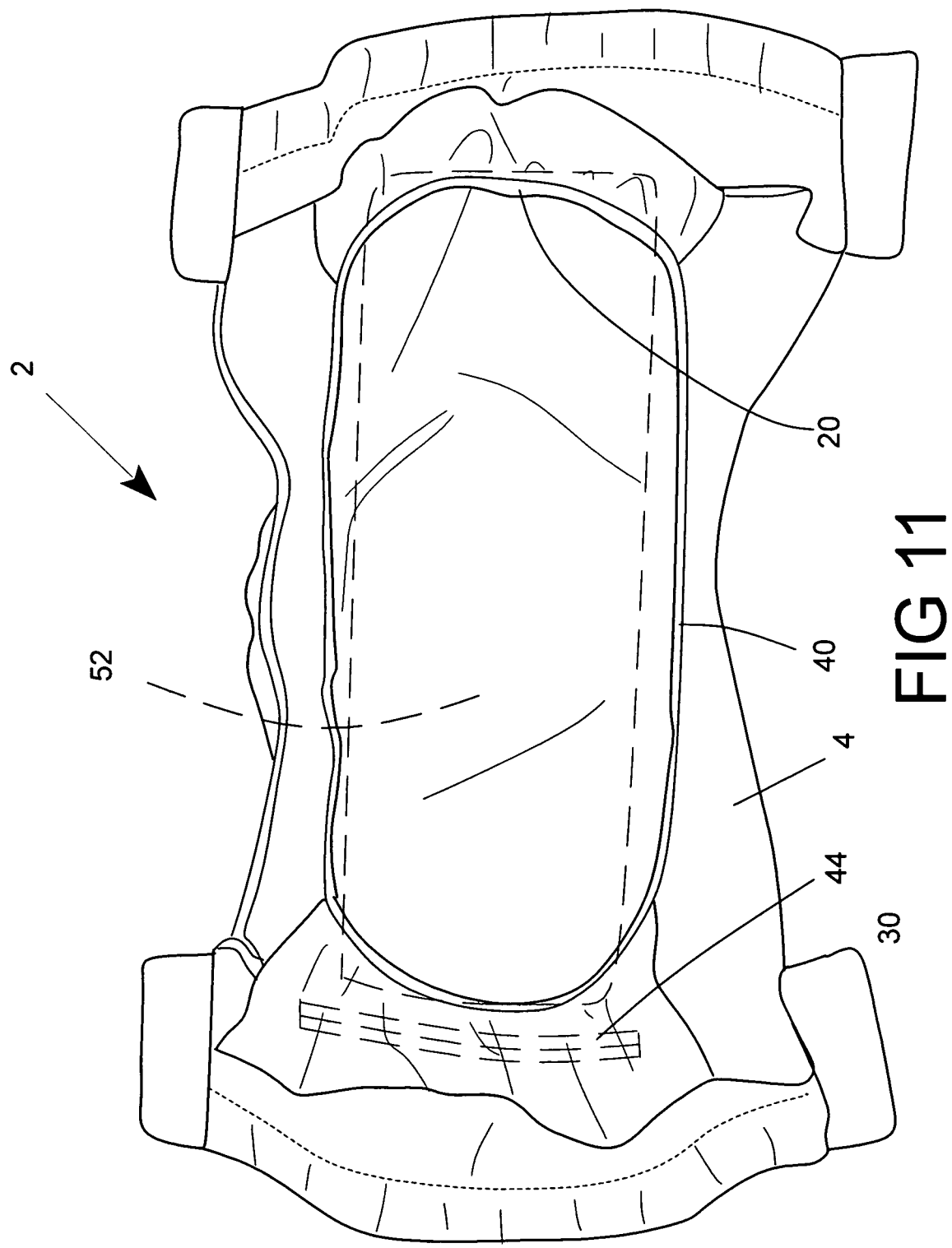
FIG. 11 is a view of another embodiment having all of the same parts as the embodiment of FIG. 9, but also including a hidden pocket for insertion of a second removable fluid absorbent pad through an opening that is normally covered by the cuff.
Figure 12:
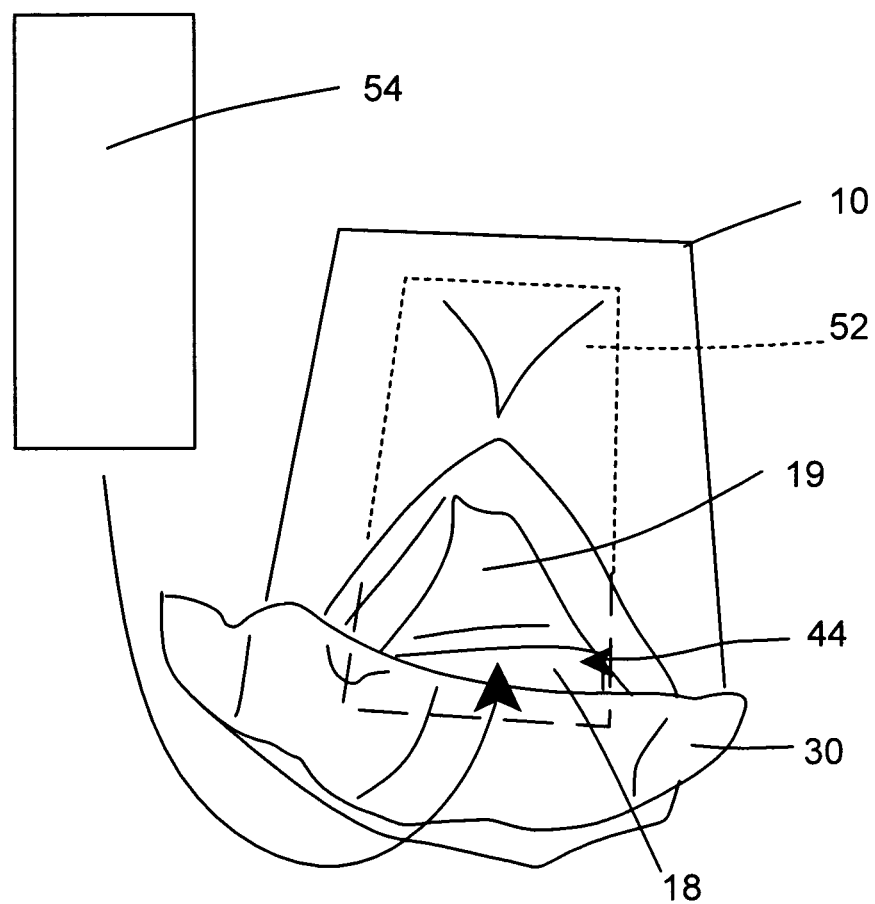
FIG. 12 is a view illustrating how a second removable fluid absorbent pad can be inserted through the opening in the sling that would be employed in FIG. 11.
Figure 15A:
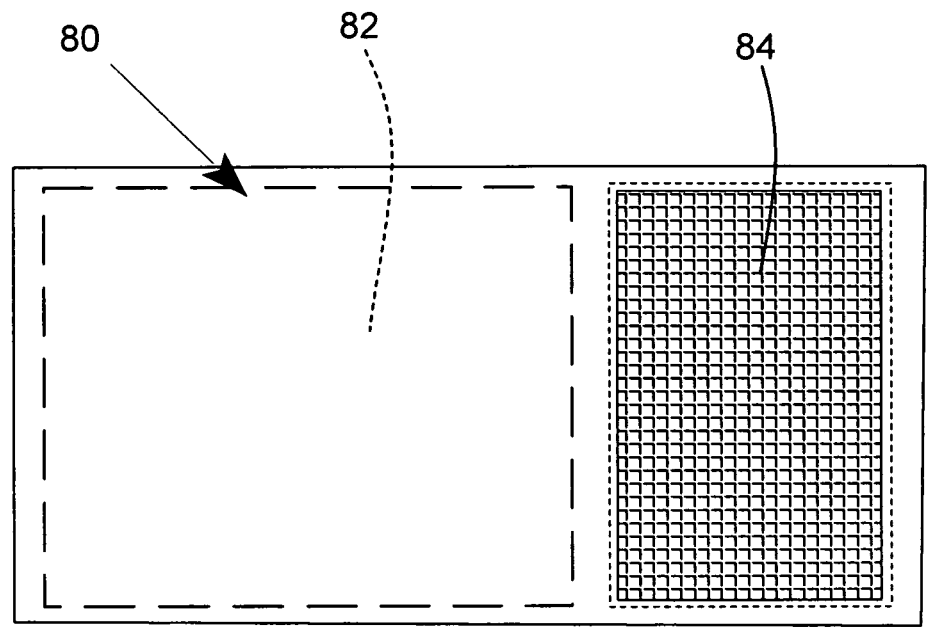
FIGS. 15A and 15B are views of an extender pad that can be used with the fasteners shown in FIGS. 14A-14D.
Figure 15B:
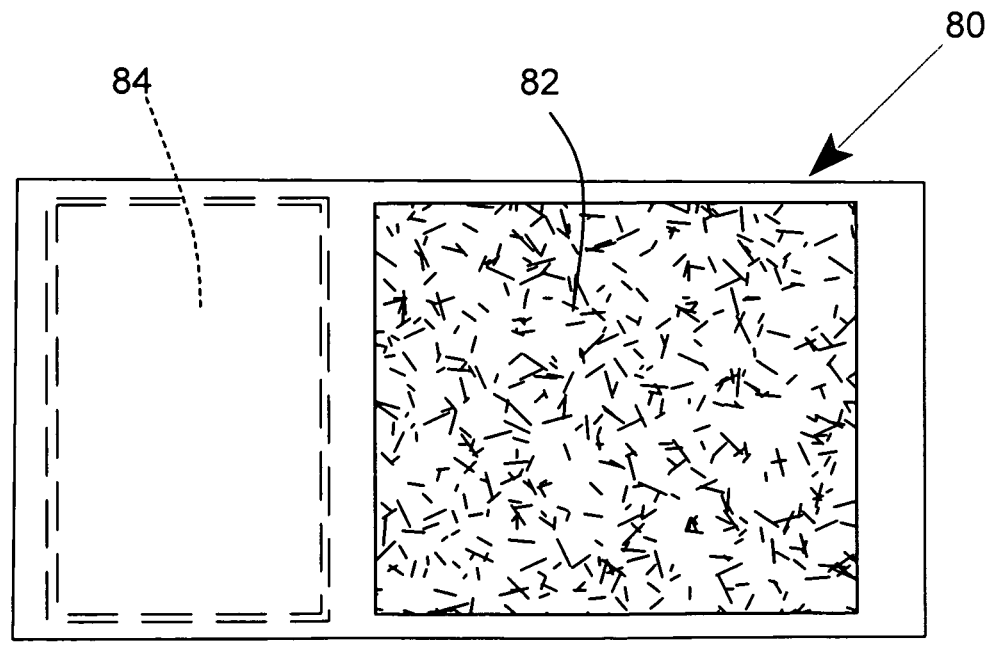

Another embodiment in which an auxiliary fluid absorbent insert pad 54 can be employed is shown in FIG. 11. This version also employs a sling that has two layers, a main waterproof layer 18 and a second or inner sling layer 19. However, a slot or opening 44 is formed in the inner sling later 19, and the cuff 30 would cover this opening 44 after the auxiliary fluid absorbent insert pad 54 is inserted between the two sling layers 18 and 19. FIG. 12 shows a sling 10, including two layers 18, 19 and an opening 44, before this sling is attached to an outer shell 4 to form the diaper of FIG. 11. It would be possible to use such an auxiliary removable pad 54 in configurations in which an internal pad 52 was also attached to the inner sling layer 19. Since the auxiliary insert pad 54 would be inserted behind the rear pocket 22, a removable fluid absorbent pad 50 could also be used with an auxiliary insert pad 54. In other words the configuration of FIG. 11 could be used with from one to three separate fluid absorbent pads providing a great deal of flexibility as well as providing extra safety of emergencies.

One removable fluid absorbent pad 500 that could be employed in the versions of sling 10 depicted herein is shown in FIG. 13. The fluid absorbent pad 50 of this embodiment comprises two side absorbent sections 62 and a central section 64. Gussets 66 extend on each side of central section 64 between sections 62 and 64. The sections 62 and 64 can be fabricated from the same material or different fluid absorbent materials can be employed in each section, depending upon the desired use. The gussets 66 are flexible so that the three pad sections can be folded when inserted into the sling 10. Gussets 66 can be fabricated from a fluid resistant material to aid in preventing lateral dispersion of moisture. Other pads, including single layer pads can also be used with slings 10. The auxiliary removable fluid absorbent pad 54 would normally comprise a single layer of fluid absorbent material so that pad 54 can be more easily inserted between the sling layers 18 and 19.

The diaper 2 of the embodiments of FIGS. 1-12 can be fastened around the wearer's waist by the use of diaper hook fastener members or tabs 70 and diaper loop fastener members or tabs 60. In the preferred embodiment of these fastener members, a hook fastener member is used on the front of the diaper 2 and a loop fastener member 60 is used on the rear of the diaper 2. The loop fastener member 60 comprises a look fastener mounted on a rectangular piece of material extending from the rear sides of the diaper. Other than the rectangular configuration of this loop fastener, with the long side extending vertically, the loop fastener is of generally conventional construction. The hook fastener member 70 does differ because it uses a hook material that has sharp edges and corners that can irritate or injure the wearer if shape edges come into contact with skin. For example, hook fasteners, commonly referred to as mushroom hooks can have such sharp corners that they have not been considered suitable for use in undergarments. Fabrication of the hook fastener member 70 is shown in FIGS. 14A-14B. The hook fastener member 70 is fabricated as a subassembly prior to being attached to the side of a diaper. FIG. 14A shows that the two parts of the hook fastener member 70 are a rectangular piece of hook fastener 72 and a cloth substrate 74 on which the hook fastener 72 is to be mounted. FIG. 14B shows that the hook fastener member is attached to the cloth member 74 only after the edges of the hook fastener 72 are first folded over all four sides of the rectangular hook fastener 72. Folds on the sides can overlap folds on the top and bottom, or the overlap can be the reverse. A seam surrounding the hook fastener goes through the overlap on all four sides. Next the cloth member is folded over the hook fastener 72 to cover the fastener, as shown in FIG. 14. The two layers of cloth are then stitched along three sides, leaving one side open. The layers of cloth are then reversed through the fourth open side so that the hook fastener 72 is on and exposed surface and the cloth member 74 is then sewn to the sides of the diaper.

The rectangular configuration of the hook fastener member 70, with the longer side being vertical provides a secure attachment to a corresponding loop fastener member on the opposite end of the diaper 2 and sling 10. This rectangular fastener shape also facilitates use of extension members 80 of the type shown in FIGS. 15A and 15B that can be employed on opposite sides of the diaper 2. Extension member 80 can be attached between the diaper hook and the loop fastener members directly to the diaper to extend the waistline of the diaper, so that it is suitable for use with a person having a larger waist. The ability to easily adjust the length is especially critical for incontinent individuals using these garments, because their weight, and waistline, can fluctuate significantly. The extension fasteners 80 have a rectangular hook fastener member 84 on one side of and on one surface of the cloth backing also forming the rectangular extension 80. Hook fastener member 84 can have the same size and shape as the hook fastener 72 on the hook fastener member 70, since both will be used to mate with the loop fastener member attached directly to the diaper. The extension loop fastener 82 is located on the opposite surface and the opposite side of the extension fastener member 80, and this loop fastener 82 will be wider than the hook fastener 84 and the diaper hook fastener 72. This will allow the loop fastener 84 to be adjustable relative to the hook fastener 72 on the diaper fastener member 70, so that when the extension member 80 is employed, almost any waist dimension can be achieved by simply adjusting the position of the loop fastener 82 relative to the diaper hook fastener member 72.

Numerous variations of these protective undergarments and their associated components are of course possible. For example, the main embodiments of this invention depict a sling, including a cuff, that is used on a diaper. Other embodiments can employ the same sling and cuff configuration with another type of garment. For example, the outer shell of a diaper could be an outer shell or outer garment comprising a brief or training pants. Alternatively the cuff can be used at the front of the protective undergarment, where it would preferably be fabricated from a fluid resistant material. One of ordinary skill in the art could make such modifications, and this invention is therefore defined by the following claims and is not limited to the details of the representative embodiments depicted herein.

I claim:

1. A protective undergarment comprising:
    an outer shell having a waistband and a bumper at a front end and a rear end of the outer shell, each bumper extending the width of the protective undergarment;
    a sling attached to the outer shell along a front end and along a rear end of the sling, sides of the sling being unattached to the outer shell;
    pockets formed on the front and rear ends of the sling, the pockets configured to retain opposite ends of a removable fluid absorbent pad extending along an exposed surface of the sling;
    one of the pockets being formed between a cuff and a main sling layer, wherein the cuff includes two cuff side edges extending between an outer cuff edge and an inner cuff edge, the cuff being stitched to the main sling layer along the outer cuff edge and the two side cuff edges with the inner cuff edge being unattached to the main sling layer to form the one pocket, closed along three sides of the pocket and open along a fourth side of the pocket, so that one end of the removable fluid absorbent pad can be inserted into the pocket formed between the cuff and the main sling layer, wherein:

the pocket formed on the rear end of the sling is formed by portions of the cuff and main sling layer, the cuff of the pocket formed on the rear end of the sling is directly attached to the bumper on the rear end of the outer shell;

the pocket formed on the front end of the sling is an S-pocket, the S-pocket comprising three layers of material in which the first layer of material is a fluid resistant material directly attached to the bumper on the front end of the outer shell, the third layer of material comprises a portion of the sling, and the second layer of material is disposed in between and attached to the first layer of material and the third layer of material; and the S-pocket has a different size and shape than the pocket formed on the rear end of the sling.

2. The protective undergarment of claim 1 wherein elastic extends along the inner cuff edge on the fourth side of the pocket, and along sides of the sling between the pockets.

3. The protective undergarment of claim 2 wherein the inner cuff edge is arcuate, and the elastic comprises a single elastic strip extending along the inner cuff edge and the sides of the sling.

4. The protective undergarment of claim 1 wherein the main sling layer is formed of a fluid resistant material.

5. The protective undergarment of claim 4 wherein the cuff is formed of a material that is softer to a wearer's skin than the main sling layer.

6. The protective undergarment of claim 5 wherein the cuff is formed of a fluid absorbent material.

7. The protective undergarment of claim 4 wherein the second layer material of the S-pocket comprises a fluid resistant material.

8. The protective undergarment of claim 7 wherein an internal fluid absorbent pad is positioned between the front end and rear end pockets.

9. The protective undergarment of claim 8 wherein the internal fluid absorbent pad is stitched to a portion of the sling that is not the main sling layer, so that stitches do not extend from the internal fluid absorbent pad through the main sling layer.

10. A protective undergarment comprising:
an outer shell having a waistband and a bumper at a front end and a rear end of the outer shell, each bumper extending the width of the protective undergarment;
a sling including a main sling layer and a second sling layer, the sling attached to the outer shell along a front end and along a rear end of the sling, sides of the sling unattached to the outer shell;
pockets formed at the front and rear ends of the sling configured to retain opposite ends of a removable fluid absorbent pad extending along an exposed surface of the sling, wherein the pocket formed at the rear end of the sling is formed between a cuff and the main sling layer; and
an internal absorbent pad positioned between the second sling layer and the main sling layer, the pockets unobstructed by the internal absorbent pad such that the removable fluid absorbent pad can be retained by the pockets, wherein:
the pocket formed on the rear end of the sling is formed by portions of the cuff and main sling layer, the cuff of the pocket formed on the rear end of the sling is directly attached to the bumper on the rear end of the outer shell;

the pocket formed on the front end of the sling is an S-pocket, the S-pocket comprising three layers of material in which the first layer of material is a fluid resistant material directly attached to the bumper on the front end of the outer shell, the third layer of material comprises a portion of the sling, and the second layer of material is disposed in between and attached to the first layer of material and the third layer of material; and the S-pocket has a different size and shape than the pocket formed on the rear end of the sling.

11. The protective undergarment of claim 10 wherein the main sling layer is formed of a fluid resistant material and the second sling layer is formed of a fluid permeable material.

12. The protective undergarment of claim 11 wherein the internal absorbent pad is stitched to the second sling layer.

13. The protective undergarment of claim 11 wherein the second sling layer includes an opening at one end for inserting and removing the removable fluid absorbent pad from between the main sling layer and the second sling layer.

14. A protective undergarment comprising:
an outer garment having a waistband and a bumper at a front end and a rear end of the outer garment, each bumper extending the width of the protective undergarment;
a sling attached to the outer garment along a front edge and along a rear edge of the sling, side edges of the sling not being attached to the outer garment;
pockets being formed on the front and rear of the sling, the pockets being configured to retain opposite ends of a fluid absorbent pad extending along an exposed surface of the sling;
the pocket at the rear of the sling being formed by a cuff extending over one end of the sling, wherein the cuff and sling are attached to the outer garment; wherein:
the pocket formed on the rear end of the sling is formed by portions of the cuff and main sling layer, the cuff of the pocket formed on the rear end of the sling is directly attached to the bumper on the rear end of the outer shell;
the pocket formed on the front end of the sling is an S-pocket, the S-pocket comprising three layers of material in which the first layer of material is a fluid resistant material directly attached to the bumper on the front end of the outer shell, the third layer of material comprises a portion of the sling, and the second layer of material is disposed in between and attached to the first layer of material and the third layer of material; and
the S-pocket has a different size and shape than the pocket formed on the rear end of the sling.

15. The protective undergarment of claim 14 wherein the pocket at the rear of the sling is formed by the fluid resistant main sling layer beneath the cuff, the cuff being formed by a material that is softer than the fluid resistant layer of the S-pocket.

16. The protective undergarment of claim 15, wherein the pocket at the rear of the sling is slimmer and less bulky than the pocket at the front of the sling, with the fluid absorbent pad positioned in the sling.

17. The protective undergarment of claim 14 wherein the sling and the cuff are each stitched to the bumpers at the rear of the protective undergarment.

18. The protective undergarment of claim 14 wherein the main sling layer is folded at the front end to form two inner layers of the S-shaped pocket.

19. A diaper comprising:
- an outer diaper cloth shell having a waistband and a bumper at a front end and a rear end of the cloth shell, each bumper extending the width of the protective undergarment;
- a sling including a main sling layer, the sling attached to the outer diaper cloth shell along a front end and along a rear end of the sling, sides of the sling being unattached to the outer diaper cloth shell;
- pockets formed on the front and rear ends of the sling configured to retain opposite ends of a removable fluid absorbent pad extending along an exposed surface of the sling, wherein the pocket formed at the rear end of the sling is formed between a cuff and the main sling layer;
- the outer diaper cloth shell including rectangular diaper hook and loop fastener members extending from front and rear sections of the outer diaper cloth shell, each diaper hook and loop fastener member having a longer dimension extending transverse of the waistband than in a direction along which the waistband extends, the rectangular diaper hook and loop fastener members comprising a diaper hook fastener on each side of the waistband at one end of the sling and a diaper loop fastener on each side of the waistband at the other end of the sling; and
- rectangular extension members attached to each diaper hook and loop fastener member comprising hook or loop members on one surface and cloth backing on the other surface, each of the rectangular extension members with the loop members being wider than the respective extension member with the hook members.

20. The diaper of claim 19 wherein edges and corners of the diaper hook fastener and the extension hook fastener are overlapped by cloth folds formed from cloth respectively forming the outer diaper cloth shell and the extension cloth backing so that said edges and corners are not exposed.

* * * * *